US005238720A

United States Patent [19]

Volkman

[11] Patent Number: 5,238,720

[45] Date of Patent: Aug. 24, 1993

[54] MOLDED-IN LABEL WITH REMOVABLE PORTION

[75] Inventor: James B. Volkman, Appleton, Wis.

[73] Assignee: Menasha Corporation, Neenah, Wis.

[21] Appl. No.: 695,369

[22] Filed: May 3, 1991

[51] Int. Cl.[5] .......... A61F 13/02

[52] U.S. Cl. .......... 428/40; 40/306; 40/310; 40/630; 264/509; 264/510; 283/81; 283/101; 428/34.2; 428/354; 428/355

[58] Field of Search .......... 428/34.2, 40, 355, 354, 428/343; 264/509, 510; 40/630, 306, 310; 283/81, 101

[56] References Cited

U.S. PATENT DOCUMENTS

| | | | |
|---|---|---|---|
| 3,108,850 | 10/1963 | Brandt | 264/509 |
| 4,479,838 | 10/1984 | Dunsirn et al. | 156/247 |
| 4,528,055 | 7/1985 | Hattemer | 428/40 |
| 4,601,926 | 7/1986 | Jabarin | 264/509 |
| 4,729,864 | 3/1988 | Chang | 264/509 |
| 4,846,504 | 7/1989 | MacGregor | 283/101 |
| 4,883,697 | 11/1989 | Dornbusch | 40/310 |
| 4,904,324 | 2/1990 | Heider | 156/214 |
| 5,024,014 | 6/1991 | Swierczek | 40/310 |
| 5,031,938 | 7/1991 | Instance | 283/81 |

FOREIGN PATENT DOCUMENTS

| | | | |
|---|---|---|---|
| 5600 | 1/1978 | Japan | 283/81 |
| 1158464 | 7/1969 | United Kingdom | 283/81 |

OTHER PUBLICATIONS

Pp. 76–82 from Packaging Digest entitled "Package Manufacturing".

*Primary Examiner*—George F. Lesmes
*Assistant Examiner*—Nasser Ahmad
*Attorney, Agent, or Firm*—Quarles & Brady

[57] ABSTRACT

A multi-layer label to be applied to a blow molded plastic container during the molding process, wherein a removable portion of the label can be easily removed, yet the label provides a smooth and attractive label surface after being molded to the container. Preferably the label includes a removable top sheet composed of a latex impregnated paper releasably adhered to the base sheet at a side opposite the plastic container. The top sheet is adhered to the base sheet by a dry residue adhesive in a manner which allows uniform and simultaneous shrinkage to occur between the base sheet and the top sheet as the molded container cools and shrinks, while also allowing subsequent removal of the top sheet from the base sheet, leaving a nontacky and visually unobstructed base sheet and removed section of the top sheet.

21 Claims, 2 Drawing Sheets

FIG. 1
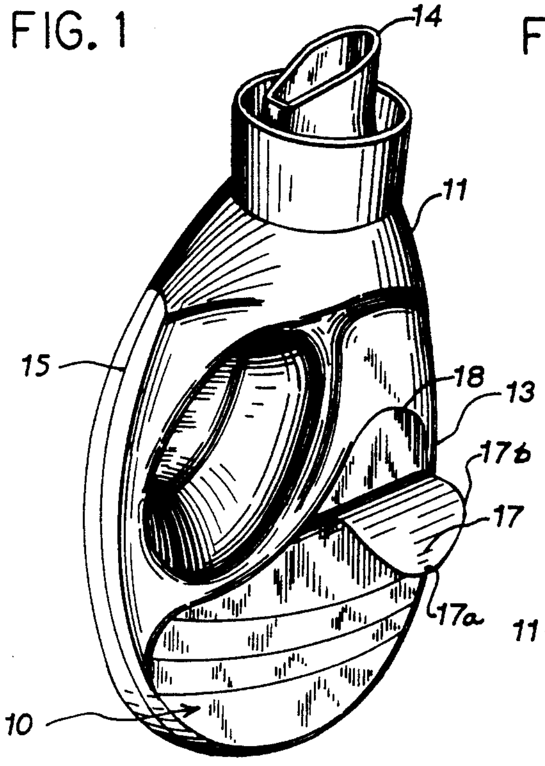
FIG. 2
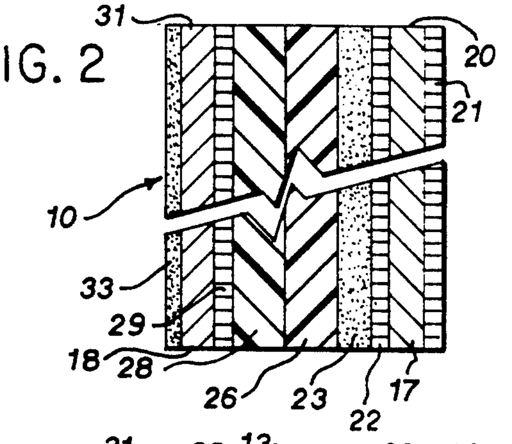
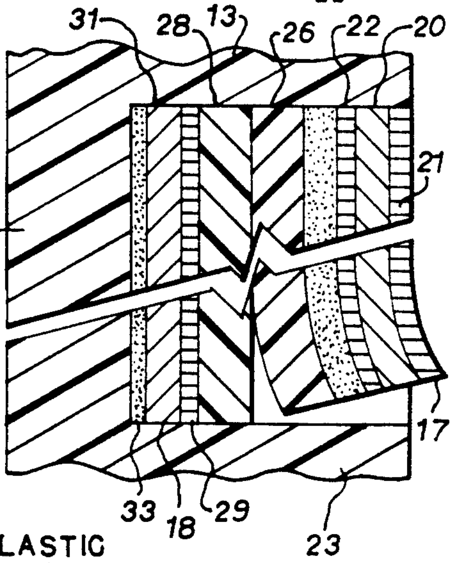
FIG. 3
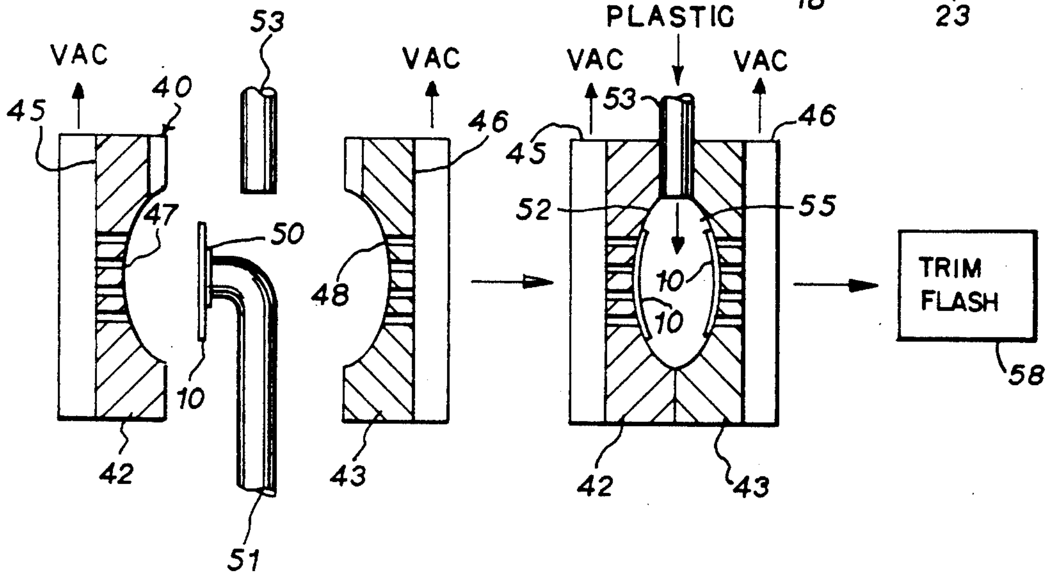
FIG. 4

MOLDED-IN LABEL WITH REMOVABLE PORTION

BACKGROUND OF THE INVENTION

This invention relates to a label of the type generally referred to as an in-mold label, which is molded into the surface of a blow-molded plastic container at the time the container is manufactured. More particularly, it relates to a two-ply label of the foregoing type in which the top ply can be easily removed from the container by a consumer, leaving the bottom ply attached to the container, with no tacky adhesive residue on either the removed top ply or on the remaining base ply.

It is known in the coupon and label art to provide a two-ply label in which a top ply is easily removable, leaving a base label attached to a substrate and no tacky residue on either ply. The top ply can be a coupon or other promotional device, and the base ply can be a printed label or can be a clear material. This type of label is described in U.S. Pat. No. 4,479,838, which is commonly assigned, and the teachings of which are incorporated herein by reference. This type of two-ply label has not previously been adapted to use on a blow-molded container where the label is molded into the surface of the container.

Previous attempts to adapt this type of two-ply label to a blow-molded container have met with problems such as those caused by the contraction of the plastic when it comes out of the mold and cools. The label, being made from a different material than the plastic of the container, does not shrink at the same rate as the container. The two plies of the label must therefore be sufficiently adaptable to this contraction to remain firmly enough in contact with each other to provide a smooth surface once the bottle has come to room temperature. At the same time, the bond between the two plies of the label must be weak enough to enable the consumer to readily remove the top ply from the bottom ply.

This invention overcomes these difficulties to provide a two-ply type label which can be molded into a blow-molded container, using standard blow molding and in-mold labelling equipment, while affording a smooth label surface on the container.

It is an advantage of the invention to provide a two-ply type label which can be molded to a blow molded container.

It is another advantage of the invention to provide a two-ply type label of the foregoing type which affords a substantially smooth label surface on the blow molded container.

It is yet another advantage of the invention to provide a two-ply type label of the foregoing type which can be molded to a blow molded container without modification to a standard blow molding machine.

It is still another advantage of the invention to provide a two-ply type label of the foregoing type which affords easy removal of the top ply from the base label.

It is another advantage of the invention to provide a two-ply type label of the foregoing type without major modifications to standard label materials.

SUMMARY OF THE INVENTION

The foregoing advantages are accomplished by the present invention wherein a label is used in conjunction with a plastic substrate such as a container and the label has a base sheet molded to the container and a separate removable portion.

A removable top portion or sheet is composed of a latex impregnated paper and is releasably adhered to the base portion or sheet at a side opposite the plastic container. The removable top sheet is adhered to the base sheet by an adhesive. The top sheet is adhered to the base sheet in a manner to allow uniform and simultaneous shrinkage to occur between the base sheet and the top sheet yet will allow easy removal of the top sheet from the base sheet in such a manner so that when the top sheet is removed from the base sheet there is no tacky residue on either sheet.

In order to achieve the foregoing goals and in a preferred manner, the peel strength between the base and top sheets is in the range of 200 to 275 gm/ 1" width.

In another preferred manner, the base sheet is composed of paper that is a 60 lb. paper and the top ply is 48 lb. paper; and the dry residue adhesive is a waterborne plasticized copolymer latex material.

In one aspect of the invention, the plastic container is a blow molded bottle, and the top removable portion of the label is a coupon.

A method of molding a label with a removable portion onto a plastic substrate is also provided as well as a label of this type for molding onto a plastic substrate.

BRIEF DESCRIPTION OF THE DRAWINGS

A better understanding of the label of this invention with a removable portion will be had by reference to the following description together with the accompanying drawings, wherein:

FIG. 1 is a perspective view of the label with a removable portion molded into a blow molded container.

FIG. 2 is a view in cross section of the label prior to its molding to the container shown in FIG. 1.

FIG. 3 is a view in cross section of the label as applied to the container shown in FIG. 1.

FIG. 4 shows diagrammatic views illustrating the method of molding the label of this invention onto the blow molded container of FIG. 1.

DESCRIPTION OF THE EMBODIMENTS

Figure 5:
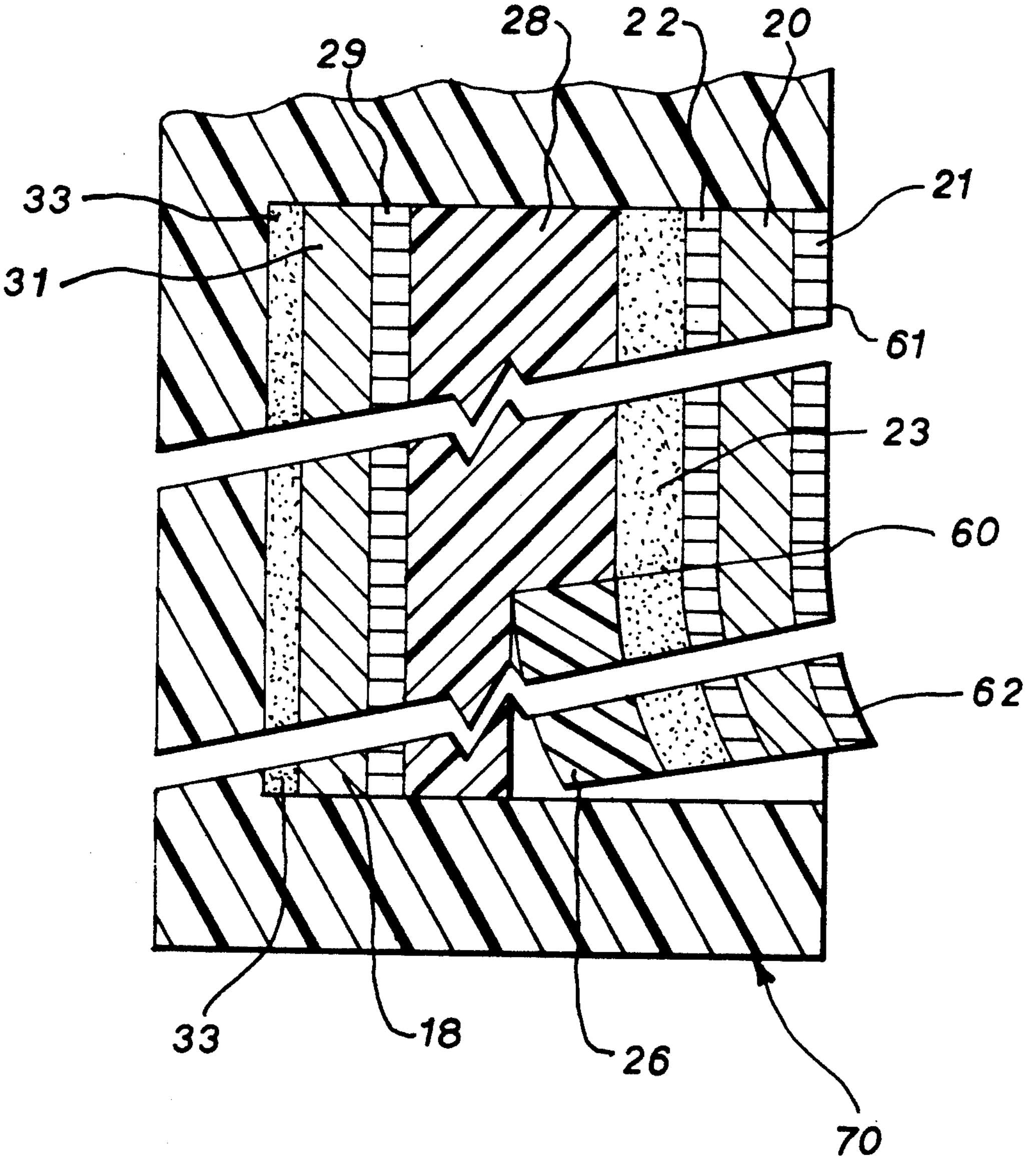
FIG. 5 is a view similar to FIG. 3 illustrating an alternative embodiment.

Referring to FIG. 1 of the drawing, the label is generally indicated at 10 as applied to a typical blow molded container or bottle 11 having a side wall 13, a pour spout 14 and a handle 15. The label 10 has a base sheet 18, which is secured to side wall 13, and a removable top sheet 17 which can serve as a coupon, instruction sheet or the like.

In the embodiment shown in FIGS. 2 and 3, the top sheet 17 of label 10 is composed of a paper layer 20 having printing 21 and 22 on both sides. In this instance, the paper layer is preferably a 48 lb. super calendered, latex-impregnated and clay-coated paper available from Kimberly-Clark Co. in Munising, Mich., and is 2.8 mil thick. The base sheet 18 is composed of a paper layer 31 having printing 29 on one side. In this embodiment, this paper layer 31 is a standard 60 lb. clay-coated in-mold label stock available from the P. H. Gladfeter Company in Springrove, Pa., and is 3 mil thick. This label stock comes with a layer of heat seal adhesive 33, such as 33P5 Norprine, available from the Morton Chemical Co., already applied to one side. This heat seal layer provides the tight bond between the label 10 and the bottle sidewall 13 when the label is applied to the bottle 11 in a standard in-mold-labeling process.

As illustrated in FIGS. 1 and 3 the top sheet 17 is removable from the base sheet 18. It has been found that this is best effected by an adhesive combination of adhesive layer 23, release material layer 26 and varnish layer 28. This combination not only allows the release of top sheet 17 from base sheet 18, but provides a transparent, non-tacky surface on the top sheet 17 and base sheet 18 when they are separated. This avoids the problems inherent with tacky adhesive residues on this type of product and allows unobstructed viewing of printed material 22 and 29 when the top sheet 17 and base sheet 18 are separated.

The adhesive layer 23 is referred to as a "dry residue adhesive" in the previously mentioned U.S. Pat. No. 4,479,838, and is preferably a plasticized copolymer water emulsion of ethylene and vinyl acetate available from the H. B. Fuller Company of St. Paul, Minn. under the designation S-3487. This material is quick setting and has good water resistance. For application, it is diluted to a viscosity as measured by a 40 reading on a Brookfield viscometer employing a number 3 spindle, at 100 speed.

The release material 26 is an alcohol based flexo-release varnish available from Production Color, Inc. in Oakwood, Ga. under the designation of PCF-3512. For application it is diluted to a viscosity of 24 seconds as measured in a No. 2 Zahn Cup.

Varnish 28 is a quick-drying semi-gloss oil can varnish available under the tradename F67053 Oil Canister from Inmont Corporation in Neenah, Wisc. For application it is diluted to a viscosity of 16 to 18 seconds as measured in a No. 3 Zahn Cup.

Top sheet 17 is produced by applying printing layers 21 and 22 on paper layer 20 using any of a number of standard printing techniques. Base sheet 18 is produced by first applying printing layer 29 on paper layer 31 using any of a number of standard printing techniques. Varnish layer 28 is then applied over printing layer 29 using an anilox roller with 200 lines per inch, a doctor blade and a transfer plate. Release material 26 is then applied over the varnish layer 28 using an anilox roller having 800 lines per inch, a doctor blade and a transfer plate. The adhesive 23 is then applied over release material 26 using an anilox roller having 120 lines per inch, a doctor blade and a transfer plate. Top sheet 17 is then applied over the adhesive 23 before the adhesive 23 has set, and base sheet 18 and top sheet 17 are then nipped together under pressure. Typically, all of the foregoing processes are performed on continuous webs of material 20 and 31, and the resulting assembly is subsequently die cut to form individual labels 10 in the shape and size desired.

FIG. 4 illustrates the process for applying the label 10 to the container 11. The label 10 is pulled from a stack of labels by means of a vacuum pad 50 with a vacuum being supplied by vacuum line 51. Label 10 is positioned between two mold halves 42 and 43 of a refrigerated mold, generally 40, having the usual vacuum passages 45, 46 and 47, 48, respectively. In the instance where two labels 10 are to be applied to the front and back of the container 11, two oppositely positioned pads such as 50 would be employed to place labels 10 inside both mold halves 42 and 43, as shown in the closed mold position of FIG. 4. With the label or labels 10 held in place, the mold halves 42 and 43 are closed and molten plastic is blown by the blow pin 53 in the form of a hot plastic parison 55 by fluid pressure against the walls of the refrigerated mold cavity 52. The molten plastic spreads to cover the inside of the cavity. The heat of the molten plastic activates the heat seal adhesive 33 on the back of the labels 10. This bonds the base sheet 18 tightly to the plastic bottle 11. The refrigeration of the mold 40 allows the molten plastic to begin hardening immediately upon contact with the walls of the mold cavity 52. When the forming process is complete, the mold halves 42 and 43 open, displaying the finished container 11 which is removed as the halves 42 and 43 part. The container or bottle 11 typically has a considerable amount of flashing around it. This flashing material is trimmed off such as indicated at 58, by use of the usual male/female dies. This process results in the plastic bottle 11 having labels 10 positioned flush with the surface of the bottle 11, as the labels 10 have been molded directly into the side wall 13 of the bottle 11, as shown in FIGS. 1 and 3.

When label 10 has been applied to the container 11 in the blow molding process, the adhesive force required to remove the base sheet 18 from the side wall 13 is much greater than that required to separate top sheet 17 from base sheet 18. Stated in another manner, the adhesion effected by combination of the adhesive 23, the release material 26 and the varnish layer 28 between the top and base sheets 17 and 18, is less than that effected between base sheet 18 and the container side wall 13 by heat seal adhesive layer 33. However, it is critical that top sheet 17 adhere to base sheet 18 strongly enough that top sheet 17 will not wrinkle when the bottle 11 cools and shrinks during the cooling process and that top sheet 17 will not prematurely release from base sheet 18 prior to separation by the consumer.

The important aspects of molding the labels 10 onto the container 11 so that the top sheet 17 will be adequately adhered to and yet can be separated from the bottom sheet 18 are the following:

1. The top sheet 17 must be of sufficient strength and flexibility to resist wrinkling and to prevent tearing during removal. The strength and flexibility are preferably provided by the use of a latex impregnated paper.

2. The bond between the bottom sheet 18 and the top sheet 17 must have a strength, measured by those skilled in the art as "peel strength," weak enough that the top sheet 17 can be readily removed from the bottom sheet 18, but at the same time strong enough that the top sheet 17 will be bonded tightly enough to the base sheet 18 so that the top sheet 17 will not wrinkle during or after the molding process as the bottle 11 cools and shrinks. This peel strength is measured by employing a standard Tag and Label Manufacturer's Institute test device wherein the label is tested at a 180° angle and a low speed of 8.5. In the embodiment, described above, a peel strength in the range of 200 to 275 gm/ 1" width results and provides the desired characteristics.

Preferably, and as described in U.S. Pat. No. 4,479,838, a selected area 17a of the top layer 17 forming a part of the margin of the top layer 17 is not adhered to the base sheet 18, as is illustrated in FIG. 1. The unadhered portion 17b forms a tab for the convenient grasping of the top portion to facilitate its removal from bottom portion 18. This can be achieved by limiting the application of adhesive 23, release material 26 and varnish layer 28 to all areas of the label other than the desired tab portion.

In some instances it may be desired to provide an in-mold label where a portion of top layer 17 is not removable. For example, it may be desired to provide a removable coupon smaller than the size of label 10. This type of coupon is shown as item 62 in FIG. 5, where the same numbers refer to the same components as previously described in conjunction with FIGS. 2 and 3. The difference between the embodiment shown in FIGS. 1, 2 and 3 and the embodiment shown in FIG. 5 is that in FIG. 5, the release material 26 is not applied over the area 61 between the adhesive layer 23 and the varnish layer 28. This prevents separation of the section 61, yet allows separation of the section 62 between the release material 26 and the varnish layer 28. A tear line 60 further facilitates separation and removal of coupon section 62.

This invention is not limited to the specific components described above. Other combinations of materials will also work, although a different peel strength may be required to achieve the desired characteristics with different materials. For example, in the preceding description the top sheet 17 was described as a latex impregnated paper with a basis weight of 48 lbs. If desired, latex impregnated papers of higher or lower basis weight could be employed, such as a 42 lb. or 60 lb. paper available from Kimberly-Clark Co. Similarly, the in-mold-label stock used in bottom sheet 18 may also be of various basis weights and can be latex impregnated if desired. It is possible to adjust the peel strength achieved by the combination of adhesive 23, release material 26 and varnish 28 by varying the amount of the various components applied to base sheet 18 or by varying the application viscosity of the components.

The adhesive 23, the release material 26 and the varnish 28 have been described in a combination which provides the preferred peel strength and release characteristics in the described embodiment. Other adhesives or varnishes or other materials, alone or in combination, may also be found to be useable in place of the described combination to achieve the desired strength and release characteristics or may be necessary to provide the required properties in different molding conditions or with different base or top sheets.

While the base sheet 18 has been described as being purchased with a previously applied heat seal adhesive layer 33, the heat seal adhesive layer 33 could be applied at the same time the label 10 is being produced. Also while the top sheet 17 is described as having opposing sides of printing 21 and 22, only one side could be printed, if desired. The top sheet 17 is preferably employed as a coupon which is removable. However it could also be employed as some other type of promotional vehicle or as an instructional panel. Neither is it necessary that any particular plastic composition be used for the container 11 to which the label 10 is applied. In this instance, it is a high density polyethylene. All that is necessary is that the resin is able to be used in a blow-molding application.

It is understood that the present invention is not limited to the particular construction and arrangement of parts illustrated and disclosed, nor to the materials specified, nor to the particular steps disclosed herein, but embraces such modified forms thereof as come with the scope of the following claims.

I claim:

1. A plastic substrate having an in-mold label with a removable portion comprising:

a plastic substrate produced in a mold;

a label attached to the substrate, the label including a base portion molded to the substrate in the mold and composed of a first layer of material;

a removable top portion composed of a second layer of material, said top portion releasably adhered to the base portion by an adhesive at a side opposite the plastic substrate; and the top portion being adhered to the base portion in a manner which allows uniform and simultaneous shrinkage to occur between the base portion and the top portion as the substrate cools and shrinks during molding, while also allowing removal of the top portion from the base portion to leave a non-tacky surface for both base sheet and top portion.

2. The invention of claim 1 wherein the top portion is a layer of latex impregnated paper.

3. The invention of claim 2 including printing on one or both of the surfaces of the paper.

4. The invention of claim 1 wherein the base portion is composed of paper.

5. The invention of claim 4 including printing on the surface of the base portion opposite the substrate.

6. The invention of claim 1 wherein both the base portion and the top portion are composed of paper.

7. The invention of claim 6 wherein the top portion is composed of a sheet of 48 lb. paper and the base portion is composed of a sheet of 60 lb. paper.

8. The invention of claim 7 wherein the peel strength between the base and top sheets is in the range of 200 to 275 gm/ 1" width.

9. The invention of claim 1 wherein the substrate is a plastic blow molded container.

10. The invention of claim 9 wherein the container is composed of a high density polyethylene.

11. The invention of claim 1 wherein the adhesive is an adhesive combination which leaves no tacky residue on the top or base portion when the top portion is removed from the base portion.

12. The invention of claim 11 wherein the adhesive combination includes a layer of dry residue adhesive, a layer of release varnish and a layer of varnish.

13. The invention of claim 12 wherein the dry residue adhesive is a water based synthetic resin.

14. The invention of claim 12 wherein the dry residue adhesive is a plasticized copolymer water emulsion of ethylene and vinyl acetate.

15. The invention of claim 1 wherein the top removable portion is a coupon.

16. The invention of claim 1 wherein the removable top portion includes a selected portion thereof at a selected part of its margin that is not adhered to the base portion, whereby the unadhered portion forms a tab for the convenient grasping of the top portion.

17. The invention of claim 1 wherein only a part of the top portion is releasably adhered to the base portion and the remainder of the top portion is permanently adhered to the base portion.

18. An in-mold label for molding to a plastic substrate and having a removable portion comprising:

a base portion composed of a first layer of sheet material, said base portion having a side for molding to the plastic substrate;

a top portion composed of a second layer of sheet material, said top portion having at least a section releasably adhered to the base portion by an adhesive at a side opposite the side for molding to the plastic substrate; and the top portion being adhered to the base portion in a manner which allows uniform and simultaneous shrinkage to occur between the base portion and the top portion as the substrate cools and shrinks during molding while also allowing removal of the top portion from the base portion to leave a non-tacky surface for both base portion and removed section of the top portion.

19. The label of claim 18 wherein the top portion is a coupon.

20. The label of claim 18 wherein the base portion and the top portion are sheets of paper.

21. The label of claim 18 wherein the substrate is a plastic blow molded container and the base portion has a heat-activated adhesive on the side to be molded to the plastic container.

* * * * *